United States Patent [19]

Kawashima et al.

[11] Patent Number: 4,803,266

[45] Date of Patent: Feb. 7, 1989

[54] 3-OXOALKYLIDENE-2-AZETIDINONE DERIVATIVES

[75] Inventors: Yutaka Kawashima, Tatebayashi; Masakazu Satoh, Konosu; Yuichi Hatada, Tokyo; Fumiko Hazato; Yoshimoto Nakashima, both of Ageo; Kaoru Sota, Tokorozawa, all of Japan

[73] Assignee: Taisho Pharmaceutical Co., Ltd., Japan

[21] Appl. No.: 104,152

[22] Filed: Oct. 5, 1987

[30] Foreign Application Priority Data

Oct. 17, 1986 [JP] Japan .................. 61-246638

[51] Int. Cl.$^4$ .................. C07D 205/08; C07D 205/10; C07D 405/04; A61K 31/395
[52] U.S. Cl. ........................................... 540/200
[58] Field of Search ......................... 540/200

[56] References Cited

FOREIGN PATENT DOCUMENTS 149419 9/1984 European Pat. Off. .

OTHER PUBLICATIONS

Buynak, Chem. Abs. 103, 178073 (1985).
Tetrahedron, vol. 41 (1985) Mori et al., pp. 375–385, "New Synthesis of β-Lactames".
Liebigs Annalen der Chemie, Heft 5, 1983, pp. 1153, 1158, 1165–1168, "Darstellung und Stereochemie von 3-(α-Hydroxybenzyl(-1, 4-diphen".
Archiv der Pharmazie, vol. 319, 1986, Bergmann et al., pp. 203–216, "Zur N- unc C-Silylierung von β-Lactamen".
Tetrahedron Letters, vol. 25, 1984, Manhas et al., p. 4735, "A Convenient Synthesis of Azetidine-2-3-Diones".

Primary Examiner—Mark L. Berch
Attorney, Agent, or Firm—Lorusso & Loud

[57] ABSTRACT

2-Azetidione derivatives represented by the following formula

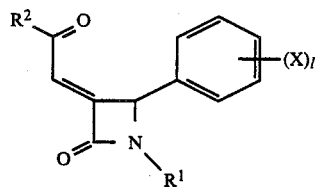

wherein X is a hydrogen atom, a halogen atom, a lower alkyl group, a lower alkoxy group, a hydroxyl group or a cyano group, l is 1 or 2, $R^1$ is a lower alkyl group, a cycloalkyl group, a 1-naphthylmethyl group, an optionally substituted phenethyl group, an optionally substituted phenyl group, an optionally substituted benzyl group or a bis(alkoxycarbonyl)ethyl group, and $R^2$ is a lower alkyl group, a lower alkoxy group, an amino group, an adamantyl group, a lower alkoxycarbonylmethyl group or an optionally substituted phenyl group, are disclosed. These compounds are useful as blood platelet aggregation inhibiting agents.

1 Claim, No Drawings

3-OXOALKYLIDENE-2-AZETIDINONE DERIVATIVES

BACKGROUND OF THE INVENTION

1. Field of the Invention

The present invention relates to 2-azetidinone derivatives having blood platelet aggregation inhibiting activity.

2. Description of the Prior Art

Although some compounds having azetidinone skeleton which show antibacterial activity have been known in the past, any azetidinone derivative showing blood platelet aggregation inhibiting activity has not been yet reported.

SUMMARY OF THE INVENTION

As a result of earnest researches to blood platelet aggregation inhibiting activity of the compounds having an azetidinone skeleton, the present inventors have found novel 2-azetidinone derivatives having blood platelet aggregation inhibiting activity, and the present invention has been completed.

An object of the present invention is to provide 2-azetidinone derivatives represented by the general formula

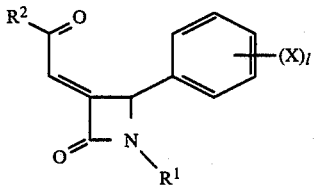

wherein X is a hydrogen atom, a halogen atom, a lower alkyl group, a lower alkoxy group, a hydroxyl group or a cyano group, l is 1 or 2, $R^1$ is a lower alkyl group, a cycloalkyl group, a 1-naphthylmethyl group, a 1-phenethyl group, 1-carboxy-2-phenethyl group, a group of the formula

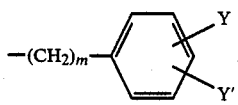

(wherein Y and Y' are the same or different and each is a hydrogen atom, a halogen atom, a lower alkyl group, a lower alkoxy group, a dimethylamino group, a carboxyl group, a dichloroacetyl group or a trifluoromethyl group, or Y and Y' together form a methylenedioxy group, and m is 0 or 1) or a group of the formula

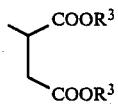

(wherein $R^3$ is a lower alkyl group), and $R^2$ is a lower alkyl group, a lower alkoxy group, an amino group, an adamantyl group, a lower alkoxycarbonylmethyl group, a group of the formula

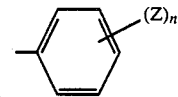

(wherein Z is a hydrogen atom, a halogen atom, a lower alkyl group, a lower alkoxy group, a phenyl group or a nitro group, and n is 1 or 2).

Other object of the present invention is to provide blood platelet aggregation inhibiting agents containing the compound of formula I.

DETAILED DESCRIPTION OF THE INVENTION

In the present invention, the term "lower alkyl group" refers to straight or branched chain alkyl group having 1 to 4 carbon atoms such as, for example, a methyl group, an ethyl group, a propyl group, an isopropyl group, a butyl group, an isobutyl group, a tert-butyl group and the like. The term "cycloalkyl group" refers to a cyclopentyl group and a cyclohexyl group. The term "lower alkoxy group" refers to those having 1 to 3 carbon atoms such as, for example, a methoxy group, an ethoxy group, a propoxy group and the like. The term "halogen atom" refers to a fluorine atom, a chlorine atom, a bromine atom and an iodine atom. The term "lower alkoxycarbonylmethyl group" refers to those such as, for example, a methoxycarbonylmethyl group, an ethoxycarbonylmethyl group and the like.

Preferred compounds of formula I are those wherein X is a hydrogen atom, $R^1$ is a benzyl group or a chlorobenzyl group, and $R^2$ is a nitrophenyl group.

The compounds of the present invention can be easily prepared, for example, by a reaction (i.e., Wittig Reaction) of a compound represented by the general formula

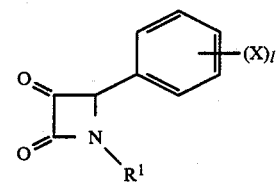

wherein $R^1$, X and l are as defined above, with a Wittig reagent represented by the general formula

wherein $R^2$ is as defined above.

Reaction solvents used in this reaction are those used in the ordinary Wittig Reaction such as, for example, benzene, ethyl ether, tetrahydrofuran, toluene, chloroform, methylene chloride, dimethoxyethane and the like. The reaction temperature is from −30° C. to the temperature of the boiling point of the solvent used, preferably from 0° C. to 30° C. The reaction time depends on the starting material, the Wittig reagent or the reaction temperature, but usually it is from 2 to 48 hours, and the reaction may be stopped after the disappearance of the starting material observed by using thin layer silica gel column chromatography.

Configuration of the oxyalkylidene substituent of all compounds of the present invention is E-form, and the configuration due to the asymmetric carbon atom at the 4-configuration is dl-form.

Some of the compounds of formula II are known, and some are new and can be prepared by the methods described in the literature [e.g., Tetrahedron Letters, Vol. 25 (No. 42), page 4733 (1984)].

It is recognized that the compounds of the present invention have excellent blood platelet aggregation inhibiting activity and very poor bleeding tendency as side-effect, and therefore, they are useful as blood platelet aggregation inhibiting agents. For the purpose, these compounds can be administered orally or parenterally in a conventional dosage form such as tablets, powders, granules, capsules, solutions, emulsions, suspensions, injectional solutions and the like, each of which can be prepared by conventional pharmaceutical practices.

The dosage used as blood platelet aggregation inhibiting agents to human depends on the age, weight or response of patient, administration route or time of administration, but usually it may be from 10 to 3000 mg per day.

The $LD_{50}$ of the compound of formula I in mouse is more than 5000 mg/kg.

Next, the following experiments illustrate concretely excellent blood platelet aggregation inhibiting activity and prolongation effect of bleeding time of the compound of the present invention.

EXPERIMENT 1 [IN VITRO TEST IN RABBIT]

Citrated blood (one volume of 3.2% sodium citrate; 9 volumes of blood) was collected from carotid artery of male, New Zealand strain house rabbit, centrifuged at 150 g for 15 minutes to give platelet rich plasma (PRP) as a supernatant, and the remaining blood was centrifuged at 1500 g for 10 minutes to give platelet poor plasma (PPP) as a supernatant. The platelet count of PRP was adjusted to $50-60 \times 10^4/\mu l$ by dilution of PPP. Blood platelet aggregation was carried out according to the method of Born [Born, G. V. R., Nature, 194, 927 (1962)]. Namely, 25 μl of the test drug, (all the test drugs were dissolved in dimethyl sulfoxide and adjusted to the desired concentration with physiological saline solution), was added to 250 μl of PRP, and the mixture was incubated at 37° C. for 3 minutes. 25 μl of the aggregation inducing substance [adenosine diphosphate (ADP); final concentration 5 μM or collagen: final concentration 5 μg/ml] was added, the mixture was measured for 5 minutes by blood platelet aggregation ability measurement apparatus (Aggricoda TM-PA-3210, Kyoto Dai-ichi Kagaku) to obtain the maximum aggregation rate, and there was calculated the concentration of the test drug ($ICP_{50}$) which brings about 50% inhibition to the maximum aggregation rate obtained by adding the aggregation inducing substance to PRP containing the solvent only.

The compound numbers in Table 1 correspond to those in the Examples described below.

TABLE 1

| Compound No. | $IC_{50}$ (× μM) ADP | Collagen | Compound No. | $IC_{50}$ (× μM) ADP | Collagen |
| --- | --- | --- | --- | --- | --- |
| 1 | 33 | 14 | 43 | 14.0 | 7.7 |
| 2 | 28 | 32 | 44 | 10.3 | 7.3 |
| 4 | 13 | 16 | 45 | 4.4 | 5.2 |
| 5 | 24 | 23.5 | 52 | 7.9 | — |
| 6 | 24 | 18 | 53 | 4.9 | — |
| 7 | 12 | 23 | 54 | 11.2 | 15.5 |
| 8 | 9.2 | 13.6 | 55 | 10.5 | 8.3 |
| 9 | 15 | 12 | 56 | 2.9 | 6.5 |
| 10 | 36 | 26 | 67 | 27.7 | 11.0 |
| 11 | >30 | 22 | 68 | 13.6 | 7.5 |
| 12 | 5.6 | 4.7 | 75 | 3.8 | 5.4 |
| 15 | 21.5 | 16.6 | 76 | 14.3 | 10.5 |
| 16 | 12.5 | 4.1 | 77 | 4.3 | 2.9 |
| 17 | 7.7 | 5.0 | 78 | 6.2 | 8.3 |
| 18 | 6.6 | 3.2 | 79 | 4.3 | 5.1 |
| 21 | 30.9 | — | 80 | 7.4 | 10.9 |
| 22 | 41.3 | — | 81 | 5.5 | 7.0 |
| 24 | 6.4 | — | 85 | 17.7 | 14.4 |
| 25 | 11.1 | 6.6 | 86 | 6.2 | 5.3 |
| 26 | 16.5 | 9.5 | 91 | 9.7 | 6.7 |
| 29 | 9.0 | 8.1 | 92 | 7.3 | 6.5 |
| 32 | 3.5 | 3.8 | 93 | 18.3 | 8.7 |
| 33 | 11.9 | 12.5 | 94 | 8.0 | 6.9 |
| 34 | 8.2 | 6.6 | 95 | 15.4 | 2.5 |
| 37 | 21.2 | 17.8 | 96 | 3.9 | 3.7 |
| 38 | 9.0 | 4.6 | 97 | 16.0 | 3.2 |
| 39 | >30 | >30 | 98 | 11.2 | 8.8 |
| 40 | 11.3 | 13.2 | 103 | 18.5 | 6.7 |
| 41 | 4.2 | 5.1 | papaverin | >100 | >100 |

EXPERIMENT 2 [PROLONGING TEST OF THE BLEEDING TIME IN MOUSE]

Six male ICR strain mice weighing 20 g for each group were administered orally with 300 mg/kg of the test drug (all the test drugs were used in the form of the suspension in 0.5% CMC). Two hours after administration, 5 mm of the tail from the top was cut under pentobarbital anesthesia, and the bleeding was observed by tapping at the cutting site with a filter paper every 15 seconds. The time when the bleeding was observed stopping for one minute is defined as the arrest point of bleeding, and the duration required from the time when the cutting was done to the arrest point of bleeding is defined as the bleeding time. The observation was carried out up to 1200 seconds. Ticlopidine was used as a positive control.

The results were shown in Table 2. The compound numbers in Table 2 correspond to those in the Examples described below.

TABLE 2

| Compound No. | Bleeding time ± standard error |
| --- | --- |
| 53 | 270.0 ± 54.08 |
| 56 | 277.5 ± 36.90 |
| ticlopidine | 1127.5 ± 72.50 (note) |
| the solvent | 305.0 ± 77.23 |

(Note) $P < 0.05$ by Mann and Whitney's U test.

The following Examples illustrate the method for preparing the compound of the present invention in more detail.

EXAMPLE 1

Preparation of (E)-3-(2-oxopropylidene)-1,4-diphenyl-2-azetidinone (Compound 1)

To a solution of 0.67 g of acetylmethylene triphenylphosphorane in 70 ml of benzene was added at room temperature under a nitrogen atmosphere a solution of 0.50 g of 1,4-diphenyl-2,3-azetidinedione in 30 ml of benzene, and the mixture was stirred overnight. After completion of the reaction, the benzene was evaporated, and the residue was applied to silica gel column chromatography (eluent; methylene chloride). The desired fractions were combined, the solvent was evaporated, and the residue was recrystallized from ethanol to give the title compound as pale yellow needles. Yield 0.32 g, m.p. 157.5°-158.5° C.

EXAMPLE 2

Following the similar procedure of that of Example 1, there were obtained the compounds 2 to 118, which were listed in Table 3 including the compound obtained in Example 1.

TABLE 3

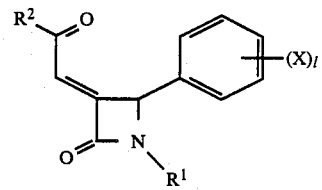

| Compound No. | $(X)_l$ | $R^1$ | $R^2$ | m.p. (°C.) |
|---|---|---|---|---|
| 1 | H | phenyl | methyl | 157.5–158.5 |
| 2 | H | phenyl | ethyl | 149–150.5 |
| 3 | H | phenyl | ethoxy | 130.5–132.5 |
| 4 | H | phenyl | phenyl | 226–227 |
| 5 | H | phenyl | p-methylphenyl | 174–177 |
| 6 | H | phenyl | p-methoxyphenyl | 227.5–228.5 |
| 7 | H | phenyl | o,p-dimethoxyphenyl | 147.5–150 |
| 8 | H | phenyl | p-fluorophenyl | 222–223 |
| 9 | H | phenyl | p-chlorophenyl | 239.5–241 |
| 10 | H | phenyl | p-bromophenyl | 250.5–256 |
| 11 | H | phenyl | p-biphenyl | 250–250.5 |
| 12 | H | phenyl | p-nitrophenyl | 235.5–236.5 |
| 13 | H | phenyl | amino | 212–213 |
| 14 | H | phenyl | 1-adamantyl | 198.5–200 |
| 15 | H | phenyl | ethoxycarbonylmethyl | 154.5–159.5 |
| 16 | H | o-methylphenyl | p-methoxyphenyl | 142–144 |
| 17 | H | o-methylphenyl | p-fluorophenyl | 140.4–141.9 |
| 18 | H | o-methylphenyl | p-nitrophenyl | 199.5–200.4 |
| 19 | H | 2,6-dimethylphenyl | p-fluorophenyl | 188–189.5 |
| 20 | H | 2,6-dimethylphenyl | p-nitrophenyl | 300 or above |
| 21 | H | o-methyl-p-chlorophenyl | p-methylphenyl | 142–144 |
| 22 | H | o-methyl-p-chlorophenyl | p-methoxyphenyl | 147–148.5 |
| 23 | H | o-methyl-p-chlorophenyl | p-fluorophenyl | 172–174 |
| 24 | H | o-methyl-p-chlorophenyl | p-nitrophenyl | 195–196 |
| 25 | H | 2-methyl-5-chlorophenyl | methyl | 149.5–151.5 |
| 26 | H | 2-methyl-5-chlorophenyl | phenyl | 145–147 |
| 27 | H | 2-methyl-5-chlorophenyl | p-fluorophenyl | 140–142 |
| 28 | H | 2-methyl-5-chlorophenyl | p-nitrophenyl | 195.5–197 |
| 29 | H | p-fluorophenyl | phenyl | 206–208.5 |
| 30 | H | p-fluorophenyl | p-fluorophenyl | 211–213 |
| 31 | H | p-fluorophenyl | p-chlorophenyl | 221.5–224 |
| 32 | H | p-fluorophenyl | p-nitrophenyl | 204.5–207 |
| 33 | H | o-fluorophenyl | p-fluorophenyl | 180.5–183 |
| 34 | H | o-fluorophenyl | p-nitrophenyl | 219.7–221 |
| 35 | H | o-chlorophenyl | p-fluorophenyl | 146–147.5 |
| 36 | H | o-chlorophenyl | p-nitrophenyl | 189–191 |
| 37 | H | 3,5-dichlorophenyl | p-fluorophenyl | 200.2–201.5 |
| 38 | H | 3,5-dichlorophenyl | p-nitrophenyl | 206 (decomposition) |
| 39 | H | p-bromophenyl | p-methoxyphenyl | 208–209 |
| 40 | H | p-bromophenyl | p-fluorophenyl | 211.5–213 |
| 41 | H | p-bromophenyl | p-nitrophenyl | 222–224 |
| 42 | H | o-methoxyphenyl | p-nitrophenyl | 219–221.2 |
| 43 | H | m-trifluoromethylphenyl | phenyl | 174–177 |
| 44 | H | m-trifluoromethylphenyl | p-fluorophenyl | 159.5–161 |
| 45 | H | m-trifluoromethylphenyl | p-nitrophenyl | 181.5–184 |
| 46 | H | p-dimethylaminophenyl | p-nitrophenyl | 168–170 |
| 47 | H | p-carboxylphenyl | p-fluorophenyl | 300 or above |
| 48 | H | p-dichloroacetylphenyl | p-fluorophenyl | 180.5–183.5 |
| 49 | H | p-dichloroacetylphenyl | p-nitrophenyl | 190.5–192.5 |
| 50 | H | benzyl | methyl | 76.5–78.5 |
| 51 | H | benzyl | phenyl | 111.5–113.5 |
| 52 | H | benzyl | p-fluorophenyl | 105–107.5 |
| 53 | H | benzyl | p-nitrophenyl | 122–126 |
| 54 | H | o-chlorobenzyl | methyl | 78–79 |
| 55 | H | o-chlorobenzyl | p-fluorophenyl | 74–76 |
| 56 | H | o-chlorobenzyl | p-nitrophenyl | 113–115 |
| 57 | H | 1(S)—phenethyl | p-nitrophenyl | 127.5–130.5 |
| 58 | H | 1-carboxy-2-phenethyl | p-fluorophenyl | 250–255 |
| 59 | H | propyl | p-fluorophenyl | 88.5–91 |
| 60 | H | propyl | p-nitrophenyl | 127.5–130.5 |
| 61 | H | cyclohexyl | methyl | 124–127 |
| 62 | H | cyclohexyl | p-fluorophenyl | 125–126.5 |
| 63 | H | cyclohexyl | p-nitrophenyl | 199–202.5 |

TABLE 3-continued

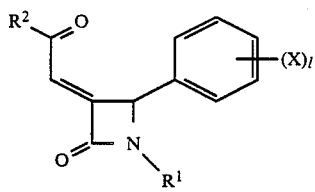

| Compound No. | (X)$_l$ | R$^1$ | R$^2$ | m.p. (°C.) |
|---|---|---|---|---|
| 64 | H | 1,2-bis(methoxycarbonyl)ethyl | p-fluorophenyl | 126–128 |
| 65 | p-methyl | phenyl | p-fluorophenyl | 208.5–211 |
| 66 | p-methyl | phenyl | p-nitrophenyl | 240.5–242.5 |
| 67 | p-ethyl | o-methylphenyl | p-fluorophenyl | 143–144.2 |
| 68 | p-ethyl | o-methylphenyl | p-nitrophenyl | 157.2–158.6 |
| 69 | o-methoxy | o-methylphenyl | p-fluorophenyl | 133–135.5 |
| 70 | o-methoxy | o-methylphenyl | p-nitrophenyl | 178–180.5 |
| 71 | m-methoxy | phenyl | p-fluorophenyl | 173.5–176.2 |
| 72 | m-methoxy | phenyl | p-nitrophenyl | 194.5–196.5 |
| 73 | 3,4-dimethoxy | phenyl | p-fluorophenyl | 164.5–169 |
| 74 | 3,4-dimethoxy | phenyl | p-nitrophenyl | 192–195 |
| 75 | p-hydroxy | phenyl | p-nitrophenyl | 166.5–167.5 |
| 76 | p-fluoro | phenyl | p-fluorophenyl | 209.5–211 |
| 77 | p-fluoro | phenyl | p-nitrophenyl | 225–226 |
| 78 | p-fluoro | o-methylphenyl | p-fluorophenyl | 157–159.5 |
| 79 | p-fluoro | o-methylphenyl | p-nitrophenyl | 193–195.5 |
| 80 | o-fluoro | phenyl | p-fluorophenyl | 191.3–192.2 |
| 81 | o-fluoro | phenyl | p-nitrophenyl | 224.8–226.7 |
| 82 | o-chloro | phenyl | p-fluorophenyl | 213.5–216 |
| 83 | p-chloro | o-methylphenyl | p-fluorophenyl | 150–151.5 |
| 84 | p-chloro | o-methylphenyl | p-nirophenyl | 180–182 |
| 85 | p-bromo | o-methylphenyl | p-fluorophenyl | 157.4–158.7 |
| 86 | p-bromo | o-methylphenyl | p-nitrophenyl | 180–180.5 |
| 87 | o-bromo | phenyl | p-fluorophenyl | 225–227 |
| 88 | o-bromo | phenyl | p-nitrophenyl | 210–212 |
| 89 | p-cyano | o-methylphenyl | p-fluorophenyl | 182.2–187.7 |
| 90 | p-cyano | o-methylphenyl | p-nitrophenyl | 180.5–183.7 |
| 91 | H | p-methylbenzyl | p-nitrophenyl | 147–148 |
| 92 | H | p-methoxylbenzyl | p-nitrophenyl | 110–112 |
| 93 | H | p-fluorobenzyl | p-nitrophenyl | 156.5–158.5 |
| 94 | H | o-methoxybenzyl | p-nitrophenyl | 146.5–148.5 |
| 95 | H | o-trifluoromethylbenzyl | p-nitrophenyl | 126–127.5 |
| 96 | H | o-fluorobenzyl | p-nitrophenyl | 116–117 |
| 97 | H | m-chlorobenzyl | p-nitrophenyl | 145–147 |
| 98 | H | p-chlorobenzyl | p-nitrophenyl | 157.5–159.5 |
| 99 | H | m-trifluoromethylbenzyl | p-nitrophenyl | 124–126 |
| 100 | H | p-trifluoromethylbenzyl | p-nitrophenyl | 107.5–109 |
| 101 | H | m-methoxybenzyl | p-nitrophenyl | 124–126 |
| 102 | H | 3,4-methylenedioxybenzyl | p-nitrophenyl | 148–151 |
| 103 | H | 2,4-dichlorobenzyl | p-nitrophenyl | 96–98 |
| 104 | H | 3,4-dichlorobenzyl | p-nitrophenyl | 145.5–148 |
| 105 | H | 1-naphthylmethyl | p-nitrophenyl | 167.5–169 |
| 106 | H | o-fluorobenzyl | p-fluorophenyl | 96–97.5 |
| 107 | H | m-methoxybenzyl | p-fluorophenyl | 108–110.5 |
| 108 | H | m-trifluoromethylbenzyl | p-fluorophenyl | 100–102 |
| 109 | H | p-trifluoromethylbenzyl | p-fluorophenyl | 136–138 |
| 110 | H | 3,4-dichlorobenzyl | p-fluorophenyl | 111–113 |
| 111 | o-methyl | benzyl | p-nitrophenyl | 111–114 |
| 112 | p-methoxy | benzyl | p-nitrophenyl | 127–128 |
| 113 | p-fluoro | benzyl | p-nitrophenyl | 118–120 |
| 114 | m-chloro | benzyl | p-nitrophenyl | 82–87 |
| 115 | p-fluoro | o-chlorobenzyl | p-nitrophenyl | 98.5–101.5 |
| 116 | p-isobropyl | o-chlorobenzyl | p-nitrophenyl | 155–156 |
| 117 | o-fluoro | o-chlorobenzyl | p-nitrophenyl | 153.5–157 |
| 118 | p-trifluoromethyl | o-chlorobenzyl | p-nitrophenyl | 115.5–121.5 |

What is claimed is:

1. 2-Azetidinone derivatives represented by the following formula:

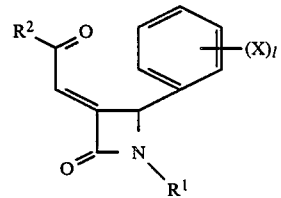

wherein:

X is hydrogen, halogen, lower alkyl, lower alkoxy, hydroxyl or cyano, l is 1 or 2, $R^1$ is lower alkyl, cycloalkyl, 1-naphthylmethyl, 1-phenethyl, 1-carboxy-2-phenethyl, a member of a group of the formula

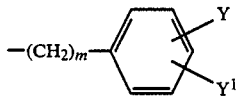

wherein Y and Y' are the same or different and each is hydrogen, halogen, lower alkyl, lower alkoxy, dimethylamino, carboxyl, dichloroacetyl or trifluoromethyl, or Y and Y' together form methylenedioxy, and m is 0 or 1 or $R^1$ is a member of a group of the formula

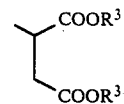

wherein $R^3$ is lower alkyl group, and $R^2$ is lower alkyl, lower alkoxy, amino, adamantyl, lower alkoxycarbonylmethyl, or a member of a group of the formula

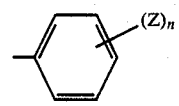

wherein Z is hydrogen, halogen, lower alkyl, lower alkoxy, phenyl or nitro, and n is 1 or 2.

* * * * *